United States Patent
Singh et al.

(10) Patent No.: US 6,359,016 B2
(45) Date of Patent: *Mar. 19, 2002

(54) TOPICAL SUSPENSION FORMULATIONS CONTAINING CIPROFLOXACIN AND DEXAMETHASONE

(75) Inventors: Onkar N. Singh, Arlington; Haresh G. Bhagat, Fort Worth, both of TX (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/865,783

(22) Filed: May 25, 2001

Related U.S. Application Data

(63) Continuation of application No. 09/636,563, filed on Aug. 10, 2000, now Pat. No. 6,284,804.
(60) Provisional application No. 60/155,942, filed on Sep. 24, 1999.

(51) Int. Cl.$^7$ .................. A61K 47/32; A61K 31/56; A61K 31/74
(52) U.S. Cl. .................. 514/772.4; 514/912; 514/169; 514/171; 424/78.04
(58) Field of Search .................. 514/772.4, 777, 514/912, 913, 914, 915, 950, 954, 955, 964; 424/427, 428, 485, 488, 78.04

(56) References Cited

U.S. PATENT DOCUMENTS

| | | | |
|---|---|---|---|
| 3,134,718 A | 5/1964 | Nobile | 167/65 |
| 4,670,444 A | 6/1987 | Grohe et al. | 514/300 |
| 4,686,214 A | 8/1987 | Boltralik | 514/179 |
| 4,844,902 A | 7/1989 | Grohe | 424/449 |
| 5,223,493 A | 6/1993 | Boltralik | 514/180 |
| 5,420,120 A | 5/1995 | Boltralik | 514/172 |
| 5,422,116 A * | 6/1995 | Yen et al. | 424/427 |
| 5,540,930 A | 7/1996 | Guy et al. | 424/427 |
| 5,679,336 A | 10/1997 | Ali et al. | 424/78.04 |
| 5,747,061 A | 5/1998 | Amselem et al. | 424/427 |
| 5,843,930 A | 12/1998 | Purwar et al. | 514/171 |
| 5,863,941 A | 1/1999 | Liedtke | 514/555 |
| 6,284,804 B1 * | 9/2001 | Singh et al. | 514/772.4 |

FOREIGN PATENT DOCUMENTS

| | | | |
|---|---|---|---|
| EP | 0 661 055 A1 | | 7/1995 |
| EP | 0 868 919 A2 | | 10/1998 |
| ES | 2065846 | | 8/1995 |
| WO | 90/01933 | | 3/1990 |
| WO | 90/01933 | * | 3/1999 |
| WO | 00/18386 | | 4/2000 |
| WO | 00/18387 | | 4/2000 |
| WO | 00/18388 | | 4/2000 |
| WO | 00/18404 | | 4/2000 |

OTHER PUBLICATIONS

Database Registry on STN, American Chemical Society, (Columbus, OH, USA).*
"Biamotil–D"Product Insert.
Ciloxan® Product Information, *Physicians' Desk Reference for Ophthalmology*, pp. 209–211 (1998).
Doshi et al., "Preparation and Evaluation of New Eye–Drops Containing a Combination of Ciprofloxacin and Dexamethasone," *Indian Drugs*, vol. 37(4); pp. 190–195 (2000).
Engel et al., "Effectiveness of Specific Antibiotic/Steroid Combinations for Therapy of Experimental *Pseudomonas aeruginosa* Keratitis," *Current Eye Research*, pp. 229–234 (1994).
Hobden et al., "Ciprofloxacin and Prednisolone Therapy for Experimental Pseudomonas Keratitis," *Current Eye Research*, vol. 11(3), pp. 259–266 (1992).
Hobden et al., "Prednisolone Acetate or Prednisolone Phosphate Concurrently Administered With Ciprofloxacin for the Therapy of Experimental *Pseudomonas Aeruginosa* Keratitis," Current Eye Research, vol. 12(5), pp. 469–473 (1993).
"Steroid and Antibiotic Solutions and Suspensions," Ophthalmic Drug Facts 1999, pp. 121–122 (1999).
Sucker et al., "Pharmazeutische Technologie," *Thieme Verlag*, p. 643–661 (1992).
Vexol® 1% (Rimexolone Ophthalmic Suspension) Product Insert.

\* cited by examiner

*Primary Examiner*—Thurman K. Page
*Assistant Examiner*—Blessing Fubara
(74) *Attorney, Agent, or Firm*—Patrick M. Ryan

(57) ABSTRACT

Suspension formulations containing dexamethasone and ciprofloxacin are disclosed. The formulations contain a nonionic polymer, a nonionic surfactant and an ionic tonicity agent, but are physically stable and easily re-suspended. The formulations are intended for topical application to the eye, ear or nose.

5 Claims, No Drawings

TOPICAL SUSPENSION FORMULATIONS CONTAINING CIPROFLOXACIN AND DEXAMETHASONE

This application is a continuation of U.S. Ser. No. 09/636,563, filed on Aug. 10, 2000 now U.S. Pat. No. 6,284,804, which claims priority to U.S. Provisional application, U.S. Ser. No. 60/155,942, filed Sep. 24, 1999.

BACKGROUND OF THE INVENTION

This invention relates to topically administrable ophthalmic and otic formulations of ciprofloxacin and dexamethasone. The formulations of the present invention are suspensions that have excellent physical stability and are characterized by their easy and ready resuspendibility. Specifically, the invention relates to stable suspension formulations of ciprofloxacin and dexamethasone that lack a nonionic tonicity agent, such as glycerol or mannitol.

Spanish Patent Application No. 2,065,846 A1 (Feb. 16, 1995) discloses topically administrable ophthalmic and otic antibiotic/steroid combination products. Examples 1–3 illustrate ophthalmic suspension formulations containing certain drug combinations with excipients including nonionic polymers and nonionic surfactants. Example 1 is a formulation of clobetasone and lomefloxacin that contains a nonionic tonicity agent (glycerin). Example 2 is a formulation of fluorometholone and norfloxacin that contains an ionic tonicity agent (sodium chloride). Example 3 is a formulation of ciprofloxacin and dexamethasone that contains a nonionic tonicity agent (mannitol).

U.S. Pat. Nos. 5,540,930 and 5,747,061 disclose topically administrable steroid suspension formulations that contain a nonionic polymer, a nonionic surfactant and a nonionic tonicity agent. The patents are directed toward "stable suspensions of water-insoluble steroid drugs of particle sizes $\leq 15$ $\mu$m, which remain in such a state so as to allow for immediate suspension, when desired, even after extended periods of settling" (see the '061 patent's Abstract). The patents are based on a finding that "[u]nexpectedly, common tonicity agents such as aqueous solutions containing 0.9% NaCl, 0.1% EDTA, or phosphate buffer, even in concentrations as low as 1 mM, can not be employed to provide stable aqueous suspensions of corticosteroids such as [loteprednol etabonate (LE)]" ('061 patent, Col. 2, lines 52–56).

The '061 patent is aimed at formulations that solved a need for "aqueous suspensions of corticosteroids such as LE which can be formulated without agglomeration" (Col. 2, lines 57–59). The '061 patent's formulations contain (A) a soft steroid such as LE present as particles preferably having a mean diameter of less than about 15 microns, (B) a nonionic polymer as a suspending agent, (C) a nonionic surfactant and (D) a nonionic tonicity agent. The '061 patent defines a "soft" drug as a biologically active chemical component characterized by predictable in vivo metabolism to non-toxic derivatives after it provides its therapeutic effect. The '061 patent teaches that "[i]t is essential that these components (A)–(D) be nonionic insofar as possible since it has now been discovered that the presence of ions is the major cause of caking" (Col. 3, lines 51–53). Nonionic diols such as glycerin or mannitol "rather than the commonly used sodium chloride" are identified as the preferred tonicity agents (see Col. 3, lines 53–56). The nonionic tonicity agent is preferably present in an amount of about 0.5 to 10% by weight.

SUMMARY OF THE INVENTION

Unless indicated otherwise, all ingredient amounts presented as a percentage are in units of weight %.

The compositions of the present invention are aqueous suspension formulations of corticosteroids (dexamethasone) that avoid agglomeration. In addition to a corticosteroid, these formulations include an antibiotic (ciprofloxacin) as a second active agent. The formulations of the present invention contain an ionic tonicity agent, but are nevertheless stable so as to be immediately and easily re-suspended when desired.

DETAILED DESCRIPTION OF THE INVENTION

The formulations of the present invention comprise a corticosteroid and an antibiotic. The corticosteroid is dexamethasone and the antibiotic is ciprofloxacin. Dexamethasone can be present in any ophthalmically or otically acceptable form having poor water solubility such that the resulting formulation is a suspension formulation. Suitable forms of dexamethasone include dexamethasone alcohol and dexamethasone acetate. Dexamethasone alcohol is the preferred form of dexamethasone. Ciprofloxacin can be present in any ophthalmically or otically acceptable form such that the ciprofloxacin ingredient is in solution in the final formulation. A preferred form of ciprofloxacin is ciprofloxacin hydrochloride, monohydrate.

The dexamethasone ingredient will comprise about 0.01–0.5% and the ciprofloxacin ingredient will comprise about 0.1–0.4% of the formulations of the present invention. The preferred amounts of dexamethasone and ciprofloxacin in the formulations of the present invention are 0.1% and 0.3%, respectively.

In addition to the active agents, the formulations of the present invention contain sodium chloride as an ionic tonicity agent. The amount of NaCl will depend on the desired tonicity for the final formulation, but will generally range from 0.1–0.9%. For ophthalmic and otic applications, the suspension formulations of the present invention preferably contain an amount of NaCl sufficient to cause the formulations to have an osmolality of about 250–350 mOsm.

The suspension formulations also contain a nonionic polymer. Many ophthalmically and otically acceptable nonionic polymers are known. These polymers include hydroxyethyl cellulose; hydroxypropylmethyl cellulose; methyl cellulose; carboxymethyl cellulose; polyvinyl pyrrolidone and polyvinyl alcohol. The preferred nonionic polymer is hydroxyethyl cellulose. The nonionic polymer will be present in the formulations of the present invention in an amount of about 0.1–0.5%. In the case of hydroxyethyl cellulose, the preferred concentration of nonionic polymer is 0.2%.

The formulations of the present invention also contain a nonionic surfactant in an amount from about 0.01–0.2%. Many ophthalmically and otically acceptable nonionic surfactants are known. Suitable nonionic surfactants include tyloxapol; polyoxyethylene sorbitan esters, such as polysorbate 20, polysorbate 60, and polysorbate 80; polyethoxylated castor oils, such as Cremaphor EL; polyethoxylated hydrogenated castor oils, such as HCO-40; and poloxamers. The preferred surfactant is tyloxapol.

If desired, the formulations may contain a quaternary ammonium halide as a preservative. Suitable quaternary ammonium halides include polyquaternium-1 and benzalkonium halides. Preferred benzalkonium halides are benzalkonium chloride ("BAC") and benzalkonium bromide. In general, the amount of the preservative ingredient will range from about 0.005–0.3%. In the preferred case where the preservative is BAC, it is preferably present at a concentration of 0.01%.

If desired, a chelating agent may also be present in the suspension formulations of the present invention. Suitable chelating agents include edetate disodium ("EDTA"); edetate trisodium; edetate tetrasodium; and diethyleneamine pentaacetate. Most preferred is EDTA. The chelating agent, if any, will typically be present in an amount from about 0.001–0.1%. In the case of EDTA, the chelating agent is preferably present at a concentration of 0.01%.

In the case of preserved or multi-dose formulations, the suspension formulations of the present invention may contain boric acid in an amount from 0.1–1.5%.

The formulations of the present invention have a pH from 3–5, preferably 4.5. pH can be adjusted with NaOH/HCl. The preferred buffering system for the formulations is a combination of sodium acetate and acetic acid. The concentration of sodium acetate will generally range from 0.015–0.06%, and will preferably be about 0.03%. The concentration of acetic acid will generally range from 0.02–0.08, and will preferably be about 0.04%.

The average particle size (mean volume basis) of the dexamethasone ingredient should be less than 10 µm to avoid irritation or discomfort. The average particle size is preferably less than 6 µm and most preferably less than 3 µm. Dexamethasone particles can be sized using known techniques, such as ball-milling, microfluidization and sonication.

The suspension formulations of the present invention are intended for topical administration to the eye, ear or nose.

The following examples are intended to illustrate, but not limit, the present invention.

EXAMPLE 1 remaining ingredients (e.g., in the case of Formulation D, the remaining ingredients are ciprofloxacin hydrochloride monohydrate, benzalkonium chloride, sodium acetate, acetic acid, sodium chloride, hydroxyethylcellulose, boric acid, edetate disodium, and purified water;
(5) steam sterilize (autoclave) the aqueous solution prepared in step (4);
(6) combine the sterile slurry obtained in step 3 to the sterile solution obtained in step 5 by aseptically pouring the slurry through a sterile sieve (to remove the beads) into the solution obtained in step 5;
(7) adjust the formulation weight to 80–90% of batch weight using sterile-filtered purified water;
(8) check the final pH and adjust to pH 4.5±0.2 by sterile-filtered sodium hydroxide or hydrochloric acid, if needed; and
(9) bring the formulation to 100% of batch weight using sterile-filtered purified water.

An alternative method of preparing Formulations A–E, especially when the dexamethasone raw material is supplied or available already meeting the desired particle size specifications, is as follows:
(1) dry heat sterilize the dexamethasone raw material (recommended specification: between 7–11 hrs. at 130–140° C. (internal powder temperature);
(2) prepare a tyloxapol solution containing the batch requirement of tyloxapol in purified water;
(3) sterilize the tyloxapol solution by passing it through a 0.2 µm filter;
(4) aseptically combine the sterilized dexamethasone with the sterilized tyloxapol solution to form a sterile slurry and stir until homogenous;
(5) prepare an aqueous solution containing the required amounts of the remaining ingredients (e.g., in the case of

|  | FORMULATION | | | | |
|---|---|---|---|---|---|
| Ingredients | A % (w/w) | B % (w/w) | C % (w/w) | D % (w/w) | E % (w/w) |
| Ciprofloxacin HCl, Monohydrate | 0.35* | 0.35 | 0.35 | 0.35 | 0.35 |
| Dexamethasone Alcohol | 0.1 | 0.1 | 0.1 | 0.1 | 0.1 |
| Hydroxyethyl Cellulose | 0.2 | 0.2 | 0.2 | 0.2 | 0.2 |
| Benzalkonium Chloride | 0.01 | 0.01 | 0.01 | 0.01 | 0.01 |
| Sodium Acetate (Trihydrate) | 0.03 | 0.03 | 0.03 | 0.03 | 0.03 |
| Acetic Acid | 0.04 | 0.04 | 0.04 | 0.04 | 0.04 |
| Sodium Chloride | 0.25 | 0.25 | 0.80 | 0.53 | — |
| Edetate Disodium | 0.01 | 0.01 | 0.01 | 0.01 | 0.01 |
| Tyloxapol | 0.05 | 0.05 | 0.05 | 0.05 | 0.05 |
| Glycerin | 1.5 | — | — | — | 2.35 |
| Boric Acid | — | — | — | 0.6 | — |
| NaOH/HCl | q.s. pH 4.5 ± 0.2 | q.s. pH 4.5 ± 0.2 | q.s. pH 4.5 ± 0.2 | q.s. pH 4.5 ± 0.2 | q.s. pH 4.5 ± 0.2 |
| Purified Water | q.s. 100 | q.s. 100 | q.s.100 | q.s. 100 | q.s. 100 |
| Osmolality (mOsm) | 272 | 99 | 274 | 286 | 290 |

*equivalent to 0.3% ciprofloxacin base

Formulations A–E were made using the following method:
(1) For a formulation batch size of 500 ml, form a slurry by combining 75 g of 3 mm zirconium beads, 12 g of tyloxapol 1.0% stock solution and 0.5 g dexamethasone alcohol in a 30 ml polypropylene milling bottle (approx. 48% of the final batch requirement of tyloxapol is used);
(2) steam sterilize (autoclave) the slurry, including beads;
(3) aseptically ball mill the sterilized slurry for 18 hrs at 50 to 55 rpm;
(4) prepare an aqueous solution containing the remaining requirement of tyloxapol and the required amounts of all Formulation D, the remaining ingredients are ciprofloxacin hydrochloride, monohydrate benzalkonium chloride, sodium acetate, acetic acid, sodium chloride, hydroxyethylcellulose, boric acid, edetate disodium and purified water;
(6) steam sterilize (autoclave) the aqueous solution prepared in step (5);
(7) aseptically combine the sterile slurry prepared in step (4) with the sterilized solution prepared in step (6);
(8) adjust the formulation weight to 80–90% of batch weight using sterile-filtered, purified water.

(9) check the final pH and adjust to pH 4.5±0.2 by sterile-filtered sodium hydroxide or hydrochloric acid, if needed; and

(10) bring the formulation to 100% of batch weight using sterile-filtered purified water.

EXAMPLE 2

Formulations A–E were tested for resuspension time in "accelerated" and "real-time" settling studies.

Accelerated settling studies were performed by subjecting 5 g of each formulation in a separate 16×125 mm flat-bottom glass tube to centrifugation for 30 minutes at 3100 rpm using an IEC CENTRA-7 centrifuge. The resuspendability of the settled material is tested by measuring the number of seconds of wrist shaking required to fully re-suspend the sediment.

Real time settling studies were performed by allowing 5 g of each Formulation in 16×125 mm flat-bottom glass tubes to undergo natural settling (under gravity) for seven days (except Formulation B, which was tested after four days). The resuspendability of the settled material is tested by measuring the number of inversions required to fully re-suspend the sediment. Table 2 contains the resuspendability results of the tested formulations.

TABLE 2

| Formulation | Accelerated Settling Resuspension Time (seconds) | Real-Time Settling Number of inversions for complete resuspension |
|---|---|---|
| A | 11 | 17 |
|   | 12 | 16 |
|   | 11 | 19 |
| B* | 6 | 16 |
|   | 7 | 16 |
| C | 13 | 12 |
|   | 16 | 13 |
|   | 19 | 11 |
| D | 7 | 12 |
|   | 9 | 13 |
|   | 6 | 11 |
| E | >60 | 18 |
|   | >60 | 26 |
|   | >60 | 19 |

*Formulation B tested after standing for 4 days; all others tested after 7 days.

EXAMPLE 3

Preservative Effectiveness Test

The antimicrobial preservative effectiveness of the polymeric quaternary ammonium compound/boric acid combination of the present invention was determined using an organism challenge test according to the methods described in the United States Pharmacopeia (USP) and European Pharmacopoeia (Ph.Eur.). Samples were inoculated with known levels of gram-positive (*Staphylococcus aureus* ATCC 6538) and gram-negative (*Pseudomonas aeruginosa* ATCC 9027 and *Escherichia coli* ATCC 8739) vegetative bacteria, yeast (*Candida albicans* ATCC 10231) and mold (*Aspergillus niger* ATCC 16404) and sampled at specified intervals to determine if the antimicrobial preservative system was capable of killing or inhibiting the propagation of organisms purposely introduced into the formulation. The rate or level of antimicrobial activity determined compliance with the USP and/or Ph.Eur. preservative efficacy standards for ophthalmic preparations.

The requirements of compendial preservative standards for ophthalmic preparations are presented below:

For Bacteria:

(*Staphylococcus aureus, Pseudomonas aeruginosa* and *Escherichia coli*)

| | 0Log Reduction of Organism Population | | |
|---|---|---|---|
| Time Pull | USP | Ph.Eur. A (Target) | Ph.Eur. B (Min) |
| 6 hours | — | 2 | — |
| 24 hours | — | 3 | 1 |
| 7 days | — | — | 3 |
| 14 days | 3 | — | — |
| 28 days | *NI | **NR | NI |
| For Fungi: | | | |
| (*Candida albicans, Aspergillus niger*) | | | |
| 7 days | — | 2 | — |
| 14 days | NI | — | 1 |
| 28 days | NI | NI | NI |

*NI = No increase at this or any following time pulls
**NR = No organism recovered
— = No requirement at this time pull The results of the preservative challenge study conducted on the formulations of Examples 1–4 are shown in Table 3. These results illustrate that, if desired, the suspension formulation of the present invention can be preserved such that it meets both the United States Pharmacopeia (USP) and European Pharmacopoeia (Ph. Eur.) minimum preservative requirements for ophthalmic and otic formulations.

TABLE 3

| | | FORMULATION | | | |
|---|---|---|---|---|---|
| Test Organism | Time | A | B | C | D |
| S. Aureus | Initial | 6.0 | 6.1 | 6.1 | 5.9 |
|  | 6 hours | 5.0 | 5.1 | 5.1 | 4.9 |
|  | 24 hours | 5.0 | 5.1 | 5.1 | 4.9 |
|  | 7 days | 5.0 | 5.1 | 5.1 | 4.9 |
|  | 14 days | 5.0 | 5.1 | 5.1 | 4.9 |
|  | 28 days | 5.0 | 5.1 | 5.1 | 4.9 |
| P. Aeruginosa | Initial | 6.0 | 6.0 | 6.0 | 6.0 |
|  | 6 hours | 5.0 | 5.0 | 5.0 | 5.0 |
|  | 24 hours | 5.0 | 5.0 | 4.7 | 5.0 |
|  | 7 days | 5.0 | 5.0 | 5.0 | 5.0 |
|  | 14 days | 5.0 | 5.0 | 5.0 | 5.0 |
|  | 28 days | 5.0 | 5.0 | 5.0 | 5.0 |

TABLE 3-continued

| Test Organism | Time | FORMULATION | | | |
|---|---|---|---|---|---|
| | | A | B | C | D |
| E. Coli | Initial | 6.0 | 6.0 | 6.0 | 5.9 |
| | 6 hours | 4.0 | 4.0 | 4.0 | 3.9 |
| | 24 hours | 4.0 | 4.0 | 4.0 | 3.9 |
| | 7 days | 4.0 | 4.0 | 4.0 | 3.9 |
| | 14 days | 4.0 | 4.0 | 4.0 | 3.9 |
| | 28 days | 4.0 | 4.0 | 4.0 | 3.9 |
| C. Albicans | Initial | 6.0 | 6.1 | 6.1 | 6.1 |
| | 7 days | 5.0 | 5.1 | 4.7 | 5.1 |
| | 14 days | 5.0 | 5.1 | 5.1 | 5.1 |
| | 28 days | 5.0 | 5.1 | 5.1 | 5.1 |
| A. Niger | Initial | 6.1 | 5.9 | 5.9 | 6.1 |
| | 7 days | 1.8 | 0.9 | 0.9 | 1.8 |
| | 14 days | 2.0 | 0.8 | 1.0 | 1.9 |
| | 28 days | 2.5 | 1.5 | 1.5 | 4.3 |
| Meets PET Requirements | | USP and Ph. Eur. B | USP only | USP Ph. Eur. B. | USP Ph. Eur. B |

Each of the Formulations listed in Table 3 passed Ph. Eur. A preservation criteria against bacteria and *Candida albicans*, but formulations lacking boric acid had difficulty passing Ph. Eur. B preservation criteria against *Aspergillus niger*. The combination of boric acid and benzalkonium chloride improved the preservative activity against *Aspergillus niger* and formulation easily met Ph. Eur. B preservative effectiveness criteria. Formulation B (without boric acid) met only USP criteria and failed the minimum Ph. Eur. Preservation requirements. Formulation C (without boric acid) met USP and Ph. Eur. B (minimum) requirements. Formulation A initially met Ph. Eur. B requirements, but showed decreased activity against Aspergillus niger when re-tested at 52 weeks. Initial and 52-week results for Formulation A are shown in Table 4.

TABLE 4

| Test Organism | Time | Initial | 52 Weeks |
|---|---|---|---|
| S. Aureus | Initial | 6.0 | 6.0 |
| | 6 hours | 5.0 | 5.0 |
| | 24 hours | 5.0 | 5.0 |
| | 7 days | 5.0 | 5.0 |
| | 14 days | 5.0 | 5.0 |
| | 28 days | 5.0 | 5.0 |
| P. Aeruginosa | Initial | 6.0 | 6.1 |
| | 6 hours | 5.0 | 5.0 |
| | 24 hours | 5.0 | 5.0 |
| | 7 days | 5.0 | 5.0 |
| | 14 days | 5.0 | 5.0 |
| | 28 days | 5.0 | 5.0 |
| E. Coli | Initial | 6.0 | 6.0 |
| | 6 hours | 4.0 | 4.0 |
| | 24 hours | 4.0 | 4.0 |
| | 7 days | 4.0 | 4.0 |
| | 14 days | 4.0 | 4.0 |
| | 28 days | 4.0 | 4.0 |
| C. Albicans | Initial | 6.0 | 6.0 |
| | 7 days | 5.0 | 5.0 |
| | 14 days | 5.0 | 5.0 |
| | 28 days | 5.0 | 5.0 |
| A. Niger | Initial | 6.1 | 6.2 |
| | 7 days | 1.8 | 1.0 |
| | 14 days | 2.0 | 1.2 |
| | 28 days | 2.5 | 1.7 |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A topically administrable aqueous suspension composition intended for application to the eye, ear or nose consisting essentially of
   a) 0.01–0.5% (wt.) dexamethasone;
   b) 0.1–0.4% (wt.) ciprofloxacin;
   c) NaCl in an amount sufficient to cause the composition to have an osmolality of about 250–350 mOsm, provided that such amount is greater than 0.3% (wt.);
   d) 0.1–0.5% (wt.) of a nonionic polymer;
   e) 0.01–0.2% (wt.) of a nonionic surfactant; and
   f) a buffer, wherein the composition has a pH of 4.5±0.2, the dexamethasone is selected from the group consisting of dexamethasone alcohol and dexamethasone acetate; and the ciprofloxacin is ciprofloxacin hydrochloride, monohydrate, and further wherein the composition optionally comprises a preservative, optionally comprises boric acid, optionally comprises a pH-adjusting agent and optionally comprises a chelating agent.

2. A topically administrable aqueous suspension composition intended for application to the eye, ear or nose consisting essentially of
   a) 0.01–0.5% (wt.) dexamethasone;
   b) 0.1–0.4% (wt.) ciprofloxacin;
   c) NaCl in an amount sufficient to cause the composition to have an osmolality of about 250–350 mOsm, provided that such amount is greater than 0.3% (wt.);
   d) 0.1–0.5% (wt.) of a nonionic polymer;
   e) 0.01–0.2% (wt.) of a nonionic surfactant; and
   f) a buffer, wherein the composition has a pH of 4.5±0.2, the nonionic polymer is hydroxyethyl cellulose, the hydroxyethyl cellulose is present in a concentration of 0.2% (wt.), the nonionic surfactant is tyloxapol, and the tyloxapol is present in a concentration of 0.05% (wt.), and further wherein the composition optionally comprises a preservative, optionally comprises boric acid, optionally comprises a pH-adjusting agent and optionally comprises a chelating agent.

3. A topically administrable aqueous suspension composition intended for application of the eye, ear or nose consisting essentially of
   a) 0.01–0.5% (wt.) dexamethasone;
   b) 0.1–0.4% (wt.) ciprofloxacin;
   c) NaCl in an amount sufficient to cause the composition to have an osmolality of about 250–350 mOsm, provided that such amount is greater than 0.3% (wt.);
   d) 0.1–0.5% (wt.) of a nonionic polymer;
   e) 0.01–0.2% (wt.) of a nonionic surfactant; and
   f) a buffer,
wherein the composition has a pH of 4.5±0.2 and the composition further comprises 0.005–0.3% (wt.) of a quaternary ammonium halide, 0.001–0.1% (wt.) of a chelating agent; and 0.1–1.5% (wt.) of boric acid, and optionally comprises a pH-adjusting agent.

4. The composition of claim 3 wherein the quaternary ammonium halide is selected from the group consisting of polyquaternium-1 and benzalkonium halides; and the chelating agent is selected from the group consisting of edetate disodium; edetate trisodium; edetate tetrasodium; and diethyleneamine pentaacetate.

5. The composition of claim 4 wherein the quaternary ammonium halide is benzalkonium chloride and the chelating agent is edetate disodium.

* * * * *